United States Patent [19]

O'Toole et al.

[11] Patent Number: 5,284,244
[45] Date of Patent: Feb. 8, 1994

[54] STERILE PACKAGE FOR SURGICAL INSTRUMENTS

[75] Inventors: Michael O'Toole, Suffern, N.Y.; Robert J. Kalinski, Milford, N.J.

[73] Assignee: Ethicon, Inc., Somerville, N.J.

[21] Appl. No.: 937,932

[22] Filed: Aug. 31, 1992

[51] Int. Cl.⁵ .................................. B65D 83/10
[52] U.S. Cl. .......................... 206/363; 206/467; 206/470; 206/564
[58] Field of Search ............. 206/363, 364, 461, 467, 206/469, 470, 564

[56] References Cited

U.S. PATENT DOCUMENTS

| | | | |
|---|---|---|---|
| 3,454,158 | 7/1969 | Tigner | 206/471 |
| 3,926,309 | 12/1975 | Center | 206/364 |
| 4,058,212 | 11/1977 | Wyslotsky | 206/470 |
| 4,499,353 | 2/1985 | Shields | 206/470 |
| 4,511,035 | 4/1985 | Alpern | 206/363 |
| 4,779,727 | 10/1988 | Taterka et al. | 206/364 |
| 4,889,231 | 12/1989 | Foote et al. | 206/363 |
| 5,131,537 | 7/1992 | Gonzales | 206/364 |
| 5,165,540 | 11/1992 | Forney | 206/363 |

*Primary Examiner*—David T. Fidei
*Attorney, Agent, or Firm*—Robert L. Minier

[57] ABSTRACT

A sterile package for surgical instruments, the package comprises upper and lower layers sealed about their periphery. A thermal formed tray is positioned between the layers. The thermal formed tray has an outwardly extending flange about its periphery. The flange is disposed between the upper plane and the lower plane of the tray.

2 Claims, 4 Drawing Sheets

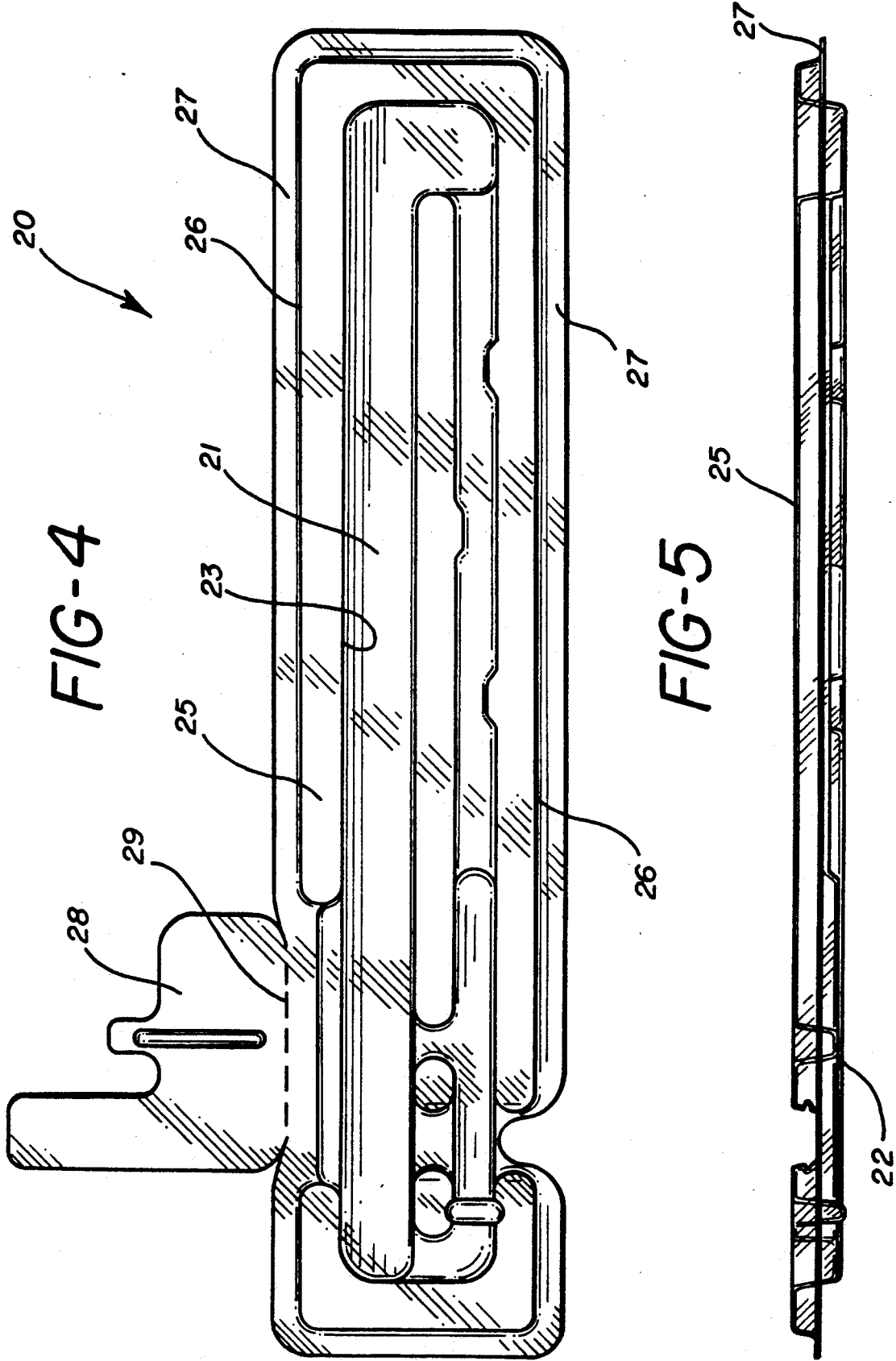

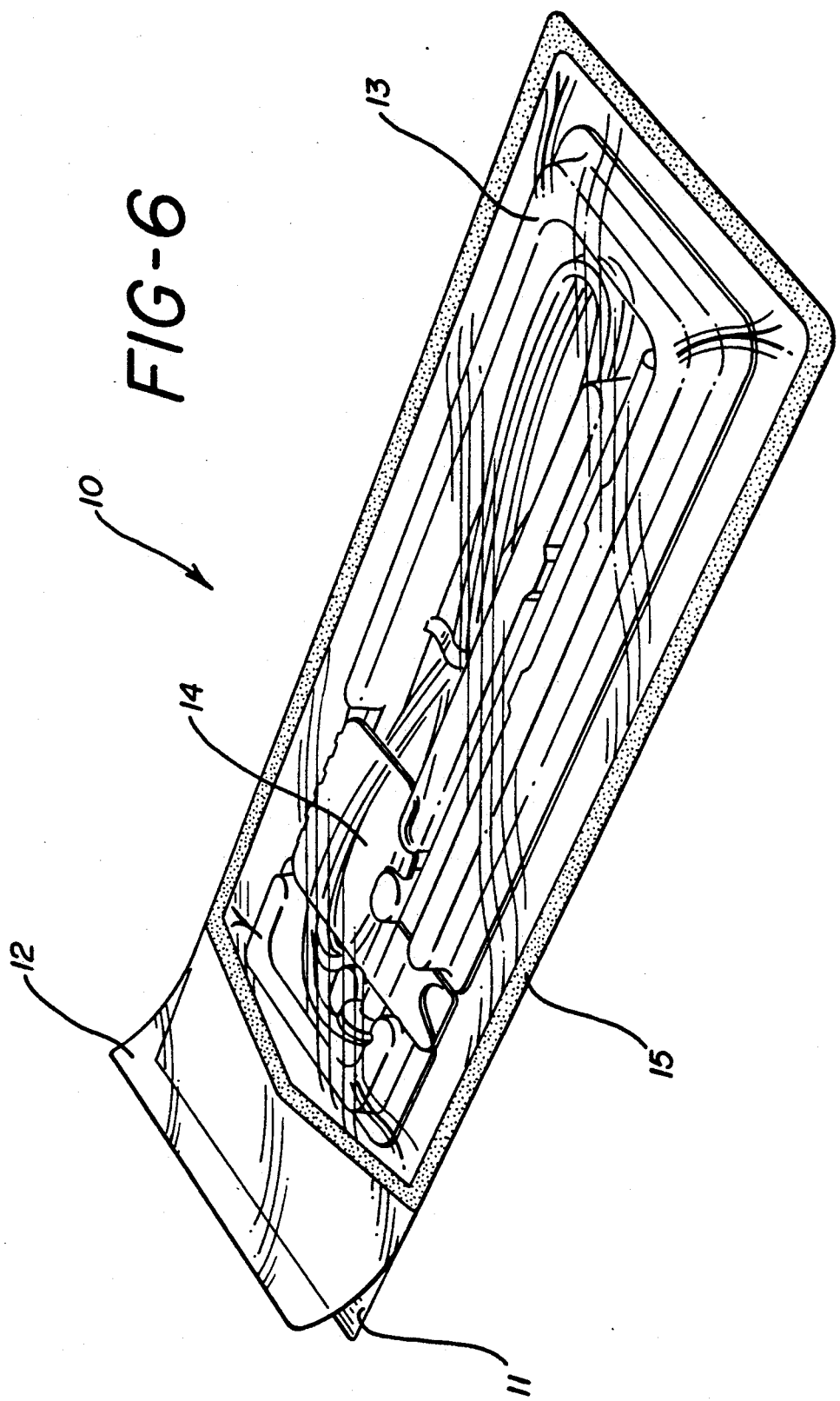

STERILE PACKAGE FOR SURGICAL INSTRUMENTS

FIELD OF THE INVENTION

This invention relates to an improved package for the sterile packaging of surgical instruments.

BACKGROUND OF THE INVENTION

In recent years, mechanical instruments for surgical use; e.g., joining tissue, closing vessels, manipulating tissue, cutting tissue, etc. have been developed. Many of these instruments are of substantial size or bulk and have some weight.

A typical package for packaging surgical products or devices in a sterile manner are heat sealed packages. These are peelable packages comprising two layers of paper, film, nonwoven fabric or combinations thereof which are generally sealed about their periphery to join them together with the surgical product disposed between the layers. Usually, the heat seal will not extend to the outer edge of the layers along one side thereof so that the layer may be readily grasped and the layers peeled apart. Such packages have gained wide acceptance because of their ease of sterilizability, their low cost and their ease of use and opening.

With the advent of the bulk or heavier instruments, it has become difficult to package such instruments in these inexpensive heat sealable packages. The instrument will tend to move around within the package during shipping and handling of the package and may well disrupt the heat seal and compromise the sterility of the instrument. A number of techniques have been developed to overcome these problems such as putting some type of stiffened insert in the heat sealed package or providing a thermal formed tray in which the instrument fits to stabilize the instrument within the package. However, such techniques cause other problems in that the package insert is usually a thin stiff member, which on movement may disrupt the heat seal. Also, the thermal formed member usually has a thin flange extending from either its upper or lower surface which if the thermal formed member moves within the heat sealed package during handling and transportation, can disrupt the heat seal and compromise the sterility of the package.

It is an object of the present invention to provide a package wherein the instrument is stabilized within the package during handling or shipping. It is another object of the present invention to provide a package which reduces the possibility of the heat seal being disrupted and the sterility of the instrument compromised during handling or shipping of the package.

SUMMARY OF THE PRESENT INVENTION

What we have discovered is an improved sterile package for surgical instruments. The package comprises an upper layer of film, paper, or the like and a lower layer of film, paper, or the like. The layers are substantially co-extensive and at least one of the layers includes a heat sealable material. The layer may be overall coated with heat sealable material or the material may be disposed about the outer circumference of the layer as desired. The layers are heat sealed together about their entire periphery. The package includes a thermal formed tray member. The tray member has at least one thermal formed cavity for holding a surgical instrument. The thermal formed tray member has an outwardly extending flange about substantially its entire periphery. The flange is disposed substantially mid-way between the top plane and the bottom plane of the thermal formed tray member to reduce the possibility of separation of the heat sealed upper and lower layers of the package.

In certain embodiments of the present invention, the thermal formed tray member includes a tab extending outwardly from the flange. The tab is foldably attached to the flange. The tab may be folded back over the tray to contain an instrument positioned in the cavity. The thermal formed member also includes a slot or a pair of slots positioned on the side of the thermal formed member opposite the tab. The slots accept the foldable tab to assist in holding an instrument within the cavity.

BRIEF DESCRIPTION OF THE DRAWINGS

FIG. 4 is a plan view of the thermo formed tray of the present invention;

FIG. 5 is a cross-sectional view of the thermo formed tray of the present invention; and FIG. 6 is a perspective view of a sterile package according to the present invention.

DETAILED DESCRIPTION OF THE DRAWINGS

Figure 1:
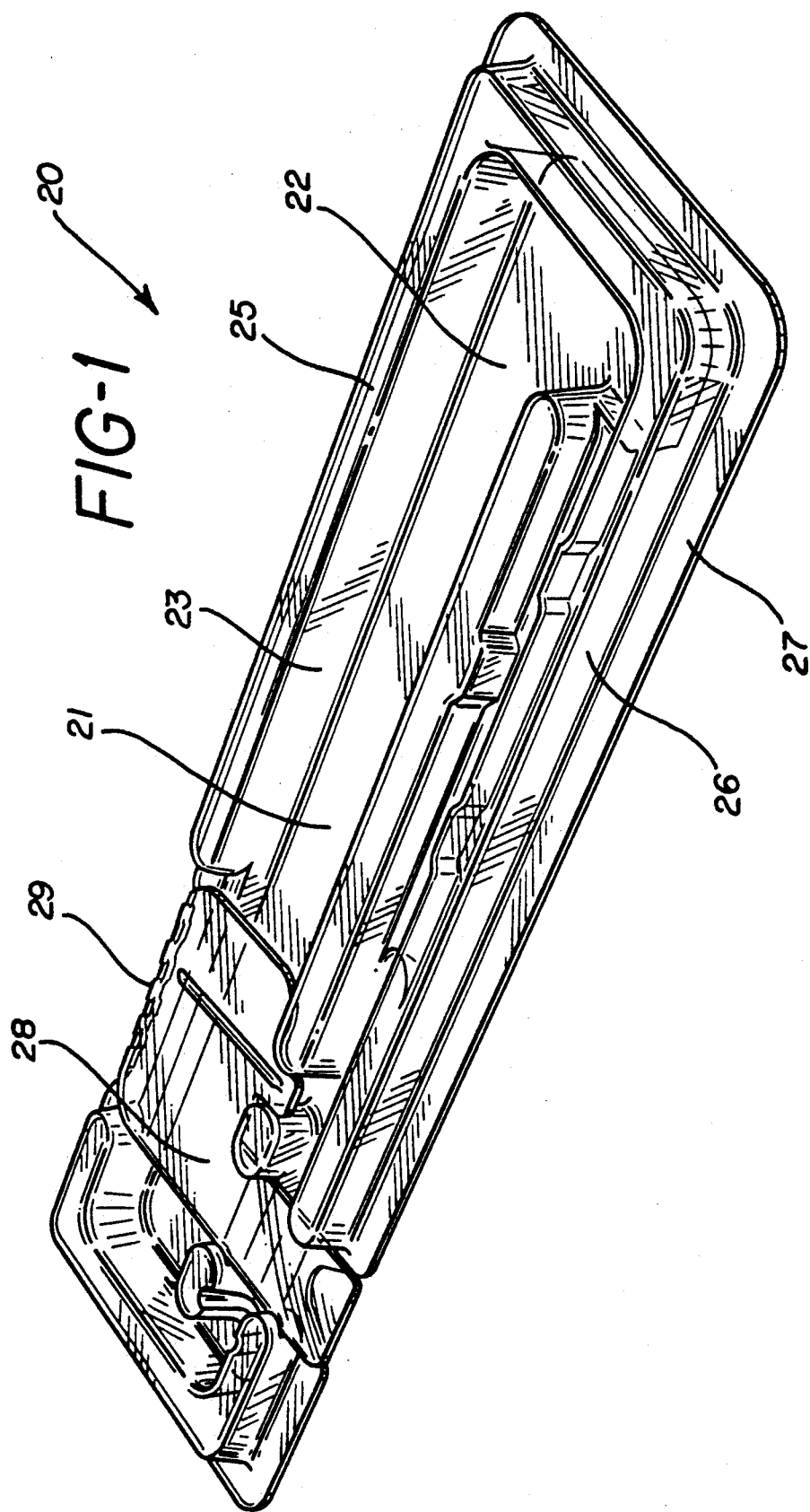
FIG. 1 is a perspective view of a thermo formed tray of the sterile package of the present invention.

Referring to the drawings, in FIG. 6, there is shown a sterile package 10 of the present invention. The package comprises a bottom or first layer 11 of film paper or the like and a second or upper layer 12 of film, paper or the like. Disposed between the layers is a thermally formed tray 13 having desired cavities disposed therein for holding one or more surgical instruments. The instruments are locked in position by the foldable hinge portion 14. The upper and lower layers are heat sealed 15 together about the periphery of the thermal formed tray. One end of the layers is left open to provide means for peeling apart the two layers to have ready access to the tray and the instruments in the tray.

Referring to FIGS. 1, 4 and 5, there is shown a thermal formed tray 20 used in the sterile package of the present invention. The tray is substantially rectangular in shape and has one or more cavities 21 disposed therein for holding surgical instruments. The tray has a bottom floor 22 and a continuous wall 23 extending upwardly from the bottom floor. The wall is disposed inwardly from the outer periphery of the tray. Disposed outwardly from the top of the wall is an outwardly extending upper surface 25. A second wall 26 extends downwardly from the outwardly extending upper surface and terminates in an outwardly extending flange 27. The bottom floor forms the bottom plane of the tray and the outwardly extending upper surface forms the top plane of the tray. About substantially the entire periphery of the tray is the flange portion. As shown in FIG. 5, the flange portion 27 is disposed approximately midway between the upper surface 25 and the bottom floor 22 of the tray. By disposing the flange portion in such a manner, not only is excellent stabilization and strength obtained in the tray, but when the tray is packaged between two layers of papers or film or the like and heat sealed therein, the possibility for the heat sealed area to become disrupted is substantially reduced. Extending from one longitudinal edge of the flange portion of the thermal formed tray is a foldable tab 28. Said foldable tab is foldable at hinge line 29 and may be folded back over the top of the thermal tray as shown in FIG. 1.

Figure 2:
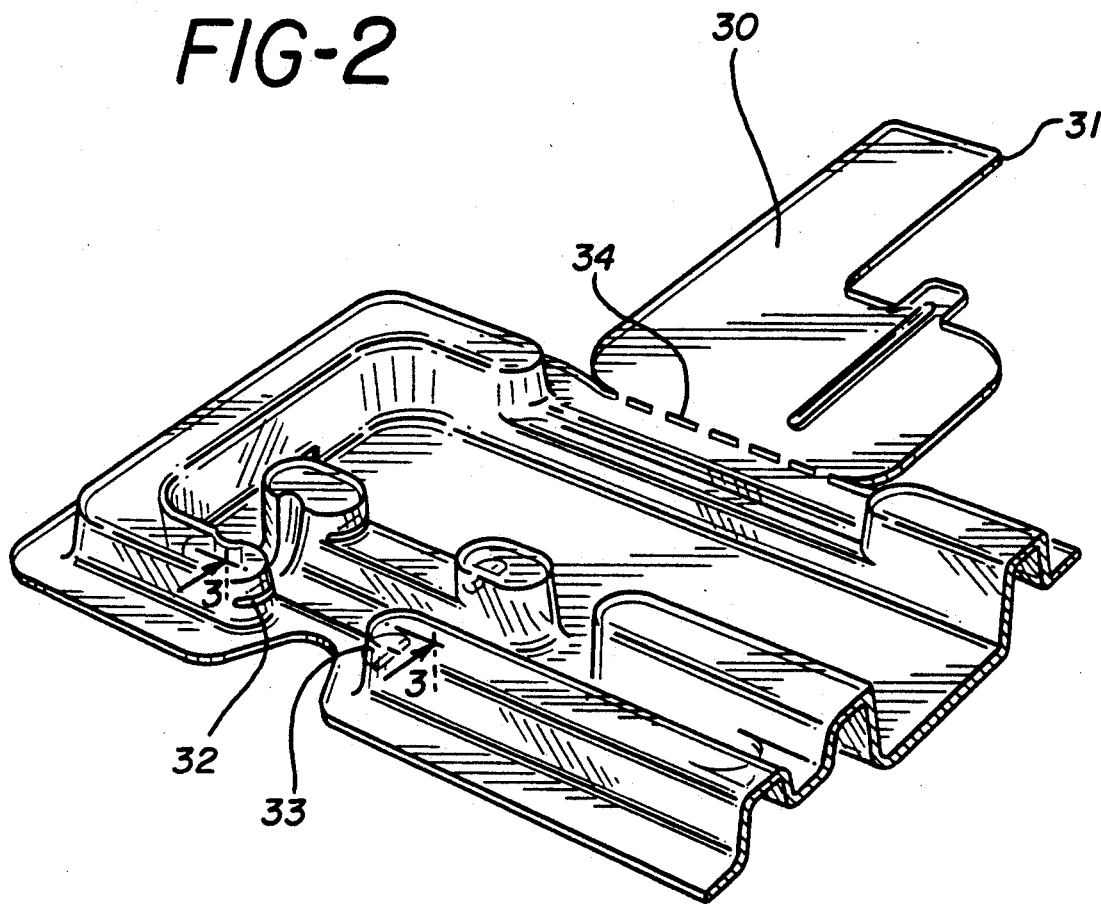
FIG. 2 is a partial cut-away perspective view showing a foldable tab used to lock an instrument in the thermo formed tray of the present invention.
Figure 3:
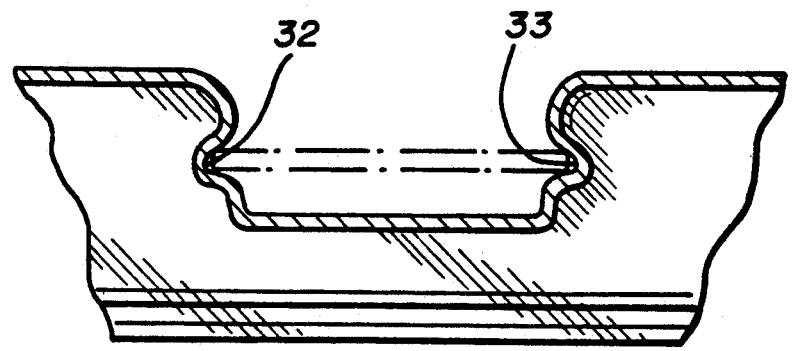
FIG. 3 is an enlarged cross-sectional view showing the slots used to contain the foldable flap.

As more clearly shown in FIGS. 2 and 3, the foldable tab 30 folds over the top of the thermal formed tray. The free end portion 31 of the tab is urged into the pair of slots 32 and 33 disposed in the formed tray. This allows instruments to be placed in the cavities and locked in place by folding the foldable tab over the top of the instruments and locking it into the slots. The hinge 34 attaching the foldable tab to the tray is made by perforating the edge of the tray so that the tab 30 may be readily folded over the top of the tray. The hinge line of the tab portion may be obtained by a die cutting process.

The thermal formed trays used in the package of the present invention may be formed using conventional thermal forming equipment and processes. The thermal forming process typically consists of an initial stage where a sheet of plastic is heated to a temperature where it is effectively moldable. The heated plastic is placed over a mold having cavities forming the structure of the tray. A vacuum is drawn through perforations in the mold to force the plastic into a configuration which conforms to the contour of the mold. The mold and the plastic sheet is cooled and the molded sheet removed from the mold. The plastic foldable hinge section may be die cut on its scored line using conventional apparatus.

The plastics which may be used to manufacture thermal formed trays include conventional plastic sheeting materials such as polyethylene terephthalate, polyvinylchloride, polypropylene, and the like. The thickness of the sheet material is typically as thin as possible but sufficiently thick to provide desired mechanical strength. The thickness may be between 0.010 inch to 0.0606 inch.

The outer packaging layers may be made from any of the well known film, paper, nonwoven fabric or combinations of the same. Bleached kraft board may be used or a polyethylene film may be used or combinations thereof. The heat sealable resin used are well known in the art. Examples of suitable heat sealed resins are the polyethylenes, polyvinylchloride and the like.

While the present invention has been described in connection with specific embodiments thereof, it will be understood that modifications and variations will be readily apparent to those of ordinary skill in the art. This disclosure and the following claims are intended to cover such modifications and variations.

What is claimed is:

1. A sterile package for sterile instruments comprising an upper layer of paper, film, nonwoven fabric or combinations of the same and a lower layer of paper, film, nonwoven fabric or combinations of the same, said layers being substantially co-extensive and being heat sealed together about the entire periphery of said layers and a thermal formed tray member disposed between said layers, said tray member having at least one thermal formed cavity for holding a surgical instrument, said tray member having an outwardly extending flange disposed about the periphery of said tray member, said flange being disposed substantially midway between the top plane and the bottom plane of said tray member to reduce premature separation of the heat sealed upper and lower layers, and a tab portion foldably attached to said outwardly extending flange, said tab portion being foldable back on said thermal formed tray member to enclose a surgical instrument disposed in said cavity.

2. A sterile package according to claim 1 wherein the tab portion is die cut.

* * * * *